US012765764B2

(12) United States Patent
Kano

(10) Patent No.: US 12,765,764 B2
(45) Date of Patent: Oct. 20, 2026

(54) EXAMINATION APPARATUS

(71) Applicant: CANON KABUSHIKI KAISHA, Tokyo (JP)

(72) Inventor: Hiroto Kano, Tochigi (JP)

(73) Assignee: Canon Kabushiki Kaisha, Tokyo (JP)

( * ) Notice: Subject to any disclaimer, the term of this patent is extended or adjusted under 35 U.S.C. 154(b) by 399 days.

(21) Appl. No.: 18/593,789

(22) Filed: Mar. 1, 2024

(65) Prior Publication Data

US 2024/0298893 A1 Sep. 12, 2024

(30) Foreign Application Priority Data

Mar. 9, 2023 (JP) ................................ 2023-036747

(51) Int. Cl.

| | |
|---|---|
| ***A61B 3/00*** | (2006.01) |
| ***A61B 3/103*** | (2006.01) |
| ***A61B 3/15*** | (2006.01) |
| ***H04N 25/62*** | (2023.01) |

(52) U.S. Cl.

CPC .......... *A61B 3/0025* (2013.01); *A61B 3/0008* (2013.01); *A61B 3/103* (2013.01); *A61B 3/15* (2013.01); *H04N 25/62* (2023.01)

(58) Field of Classification Search

CPC ..... A61B 3/0025; A61B 3/0008; A61B 3/103; A61B 3/15; A61B 3/14; H04N 25/62

See application file for complete search history.

(56) References Cited

U.S. PATENT DOCUMENTS

2009/0128671 A1* 5/2009 Kusaka ................ H04N 23/843 348/246
2017/0360297 A1* 12/2017 Yun ...................... A61B 5/0075

FOREIGN PATENT DOCUMENTS

JP 2009122524 A 6/2009

* cited by examiner

*Primary Examiner* — Travis S Fissel

(74) *Attorney, Agent, or Firm* — Canon U.S.A., Inc. IP Division

(57) ABSTRACT

An examination apparatus detecting first reflected light from a first eye of a subject and second reflected light from a second eye of the subject includes an imaging device, and a processing unit. The imaging device includes pixels each including a first photoelectric conversion unit and a second photoelectric conversion unit. The processing unit includes a unit configured to acquire a first signal based on the first reflected light entering the first photoelectric conversion units and a second signal based on the second reflected light entering the second photoelectric conversion units, a unit configured to acquire crosstalk amounts of the first and second signals based on information about positions of the first and second eyes, and a unit configured to generate correction signals based on the first and second signals and amounts of the crosstalk.

18 Claims, 9 Drawing Sheets

EXAMINATION APPARATUS

BACKGROUND

Field of the Disclosure

The present disclosure relates to an examination apparatus examining both eyes of a subject.

Description of the Related Art

Japanese Unexamined Patent Application Publication (Translation of PCT Application) No. 2018-509203 discusses an examination apparatus that examines a fixation state of a subject by projecting projection light to retinas of both eyes of the subject, and guiding reflected light from the retinas to different imaging devices by an optical system. In the examination apparatus discussed in Japanese Unexamined Patent Application Publication (Translation of PCT Application) No. 2018-509203, it is necessary to arrange two imaging lenses for guiding the reflected light from the retinas to the two imaging devices. Therefore, it is difficult to simplify the optical system.

To simplify the optical system, it is considered that an imaging device in which a plurality of photoelectric conversion units is provided in one pixel discussed in Japanese Patent Application Laid-Open No. 2009-122524 is applied to the examination apparatus examining both eyes of the subject.

However, in a case where the imaging device discussed in Japanese Patent Application Laid-Open No. 2009-122524 is applied to the examination apparatus, an error may occur on a photoelectrically-converted signal due to crosstalk of the signal caused by a neighboring photoelectric conversion unit.

SUMMARY

The present disclosure is generally directed to, in an examination apparatus detecting light reflected from both eyes, reducing influence of errors generated by crosstalk of signals obtained by an imaging device.

According to an aspect of the present disclosure, an examination apparatus detecting first reflected light from a first eye of a subject and second reflected light from a second eye of the subject includes an imaging device and a processing unit. The imaging device includes pixels each including a first photoelectric conversion unit and a second photoelectric conversion unit.

The processing unit includes a unit configured to acquire a first signal based on the first reflected light entering the first photoelectric conversion units and a second signal based on the second reflected light entering the second photoelectric conversion units. The processing unit further includes a unit configured to acquire crosstalk amounts of the first and second signals based on information about positions of the first and second eyes, and a unit configured to generate correction signals based on the first and second signals and amounts of the crosstalk.

Further features of the present disclosure will become apparent from the following description of embodiments with reference to the attached drawings.

DESCRIPTION OF THE EMBODIMENTS

Figure 1:
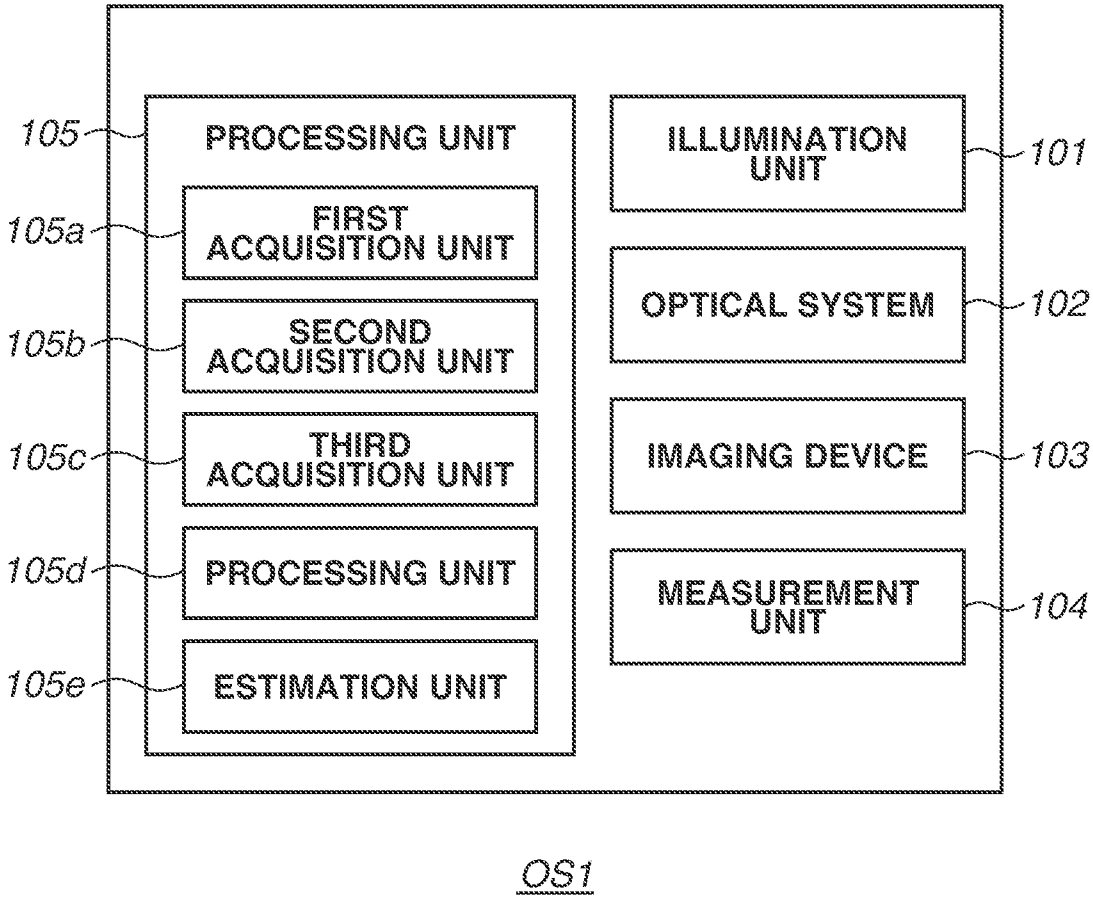
FIG. 1 is a block diagram of an examination apparatus according to a first embodiment.

Some preferred embodiments of the present disclosure will be described below with reference to drawings. The drawings may be drawn at scales different from actual scales, for convenience. In the drawings, the same members are denoted by the same reference numerals, and repetitive description is omitted. The following embodiments do not limit the disclosure according to the claims. Although a plurality of features is described in the embodiments, all of the plurality of features are not necessarily essential for the disclosure, and the plurality of features may be optionally combined.

An examination apparatus OS1 according to a first embodiment will be described with reference to FIG. 1. FIG. 1 is a block diagram of the examination apparatus OS1 according to the first embodiment. The examination apparatus OS1 includes an illumination unit 101, an optical system 102, an imaging device 103, a measurement unit 104, and a processing unit 105. In the present embodiment, an example in which examination is performed by acquiring reflected light from retinas of eyes of a subject is described. The reflected light is not limited thereto, and may be acquired from corneas, crystalline lenses, or fundus oculi.

The illumination unit 101 includes a first light source and an illumination optical system, and irradiates eyes of the subject (examinee) with light from the first light source through the irradiation optical system. The light source of the illumination unit 101 according to the present embodiment includes, for example, a display member such as a liquid crystal display and an organic electroluminescent (EL) display, and one or a plurality of point light sources such as laser diodes.

The illumination unit 101 according to the present embodiment desirably satisfies the following conditional inequality (1) in order to realize an examination with high accuracy and to reduce loads on the eyes of the subject:

$$780 \le \lambda \le 930, \tag{1}$$

where λ [nm] is a wavelength of the light emitted from the illumination unit 101.

When the wavelength λ becomes greater than an upper limit of the conditional inequality (1), an absorptance of light by water inside a living body is enhanced, and a light quantity of reflected light from the retinas may be reduced. When the wavelength A becomes lower than a lower limit of the conditional inequality (1), an absorptance of light by hemoglobin in the living body is increased, and the light quantity of reflected light from the retinas may be reduced.

Further, the illumination unit 101 preferably satisfies the following conditional inequality (1a), and more preferably satisfies the conditional inequality (1b):

$$790 \leq \lambda \leq 915, \tag{1a}$$

$$800 \leq \lambda \leq 900. \tag{1b}$$

The optical system 102 guides the reflected light from the retinas of the eyes of the subject to the imaging device 103. An optical device relating to polarization is preferably used for the optical system 102. When the optical device relating to polarization is used for the optical system 102, information about birefringence of the retinas can be acquired. The optical system 102 can simultaneously guide the reflected light (first reflected light RY1 and second reflected light RY2) from right and left eyes of the subject to the imaging device 103. An optical device may be shared between the optical system 102 and the illumination optical system, as necessary. Such a configuration makes it possible to downsize the examination apparatus.

The imaging device 103 includes a plurality of pixels IP, and receives the first reflected light RY1 and the second reflected light RY2 guided through the optical system 102. Each of the pixels IP includes a microlens ML, a first photoelectric conversion unit PD1, and a second photoelectric conversion unit PD2.

The first photoelectric conversion unit PD1 and the second photoelectric conversion unit PD2 respectively convert the guided first reflected light RY1 and the guided second reflected light RY2 into electric signals (signals). The signals photoelectrically converted by the first photoelectric conversion unit PD1 and the second photoelectric conversion unit PD2 are signals transmitting at least one of image information, luminance information, and information on polarization states. An on-chip microlens is preferably used for the microlens ML. The imaging device 103 according to the present embodiment is a photoelectric conversion device such as a charge-coupled device (CCD) sensor and a complementary metal-oxide semiconductor (CMOS) sensor.

The measurement unit 104 acquires information about a distance to the subject, as necessary. The information about the distance to the subject is information about, for example, a distance from the examination apparatus OS1 to the subject or a distance from a light receiving surface of the imaging device 103 to the subject. Alternatively, as the distance to the subject, a distance from the examination apparatus OS1 to a face or both eyes of the subject may be measured. The measurement unit 104 can acquire the information about the distance to the subject by using a known method. Examples of the method include a method based on a plurality of images including parallax, and a method of acquiring reflection (backscattering) of a laser beam.

The examination apparatus OS1 preferably includes a video image display unit that can present the subject to a user of the examination apparatus OS1. A video image display device used for the video image display unit is, for example, a liquid crystal display or a projector. The user may perform examination and the like while checking an image under processing via the video image display device. The video image display device can display video image information MT described below. Such a configuration enables the user of the examination apparatus OS1 to properly align a relative position of the examination apparatus OS1 and the subject. To temporally continuously display the subject, a moving image may be captured by an imaging unit.

The processing unit 105 includes a first acquisition unit 105*a*, a second acquisition unit 105*b*, a third acquisition unit 105*c*, a processing unit 105*d*, and an estimation unit 105*e*. The processing unit 105 generates correction signals based on the signals obtained by photoelectric conversion and crosstalk amounts of the signals, and measures a fixation state of the subject based on the correction signals. The processing unit 105 performs a step of acquiring signals based on the first reflected light RY1 entering the first photoelectric conversion units PD1 and the second reflected light RY2 entering the second photoelectric conversion units PD2, and a step of acquiring the crosstalk amounts of the signals based on information about positions of first and second eyes. The processing unit 105 further performs a step of generating the correction signals based on the signals and the crosstalk amounts. Functions as the processing unit 105 can be implemented by one or more processors such as a central processing unit (CPU) inside the examination apparatus OS1. Details of the first acquisition unit 105*a*, the second acquisition unit 105*b*, the third acquisition unit 105*c*, the processing unit 105*d*, and the estimation unit 105*e* will be described below.

Figure 2:
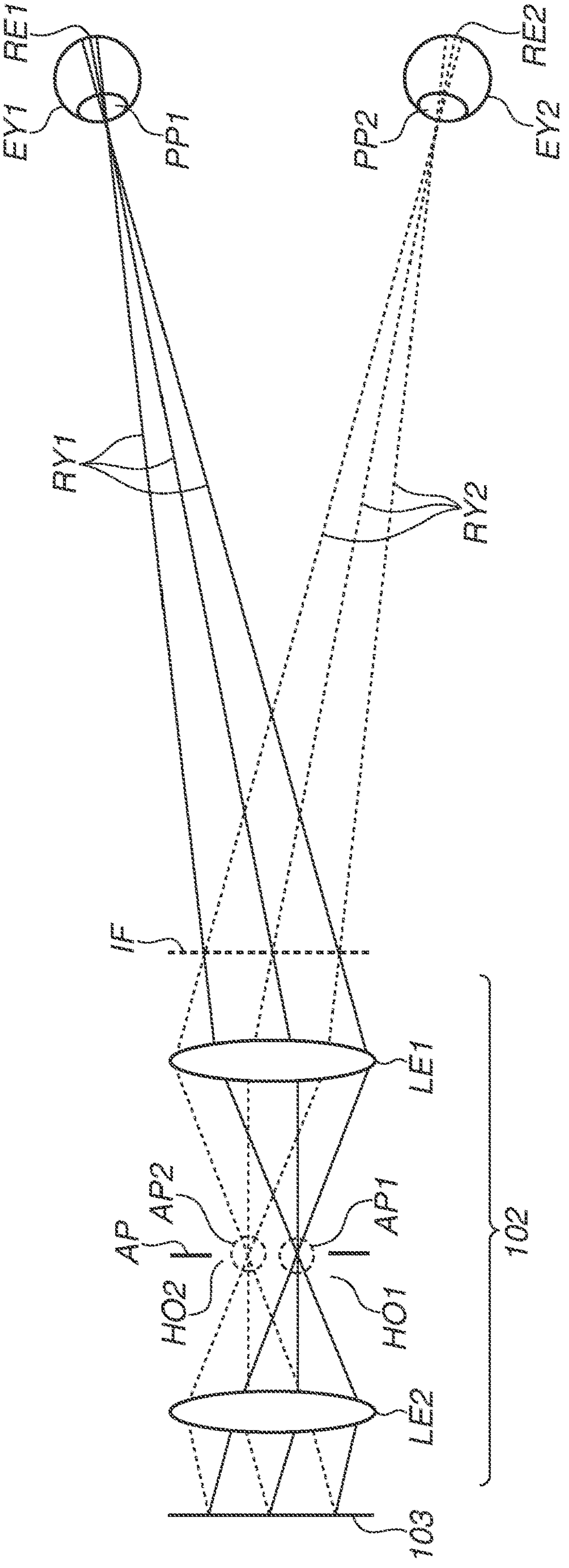
FIG. 2 is a schematic view illustrating main portions of the examination apparatus according to the first embodiment.

Relationship of the optical system 102 and the imaging device 103 with the eyes of the subject will be described with reference to FIG. 2. FIG. 2 is a schematic view illustrating main portions of the examination apparatus OS1 according to the present embodiment.

The examination apparatus OS1 includes the optical system 102 and the imaging device 103, and examines the fixation state of the subject. In FIG. 2, a first eye EY1 and a second eye EY2 are eyes different from each other. In the present embodiment, the first eye EY1 is a right eye, and the second eye EY2 is a left eye.

In FIG. 2, only the light receiving surface (imaging surface) is illustrated as the imaging device 103. Details of the imaging device 103 will be described below. The optical system 102 includes optical devices LE1 and LE2 and a diaphragm AP. In the following, relative to the optical system 102, the subject side will be referred to as an object side, and the imaging device side will be referred to as an image side. The light receiving surface of the imaging device 103 is disposed on an image plane of the optical system 102.

A solid line in FIG. 2 indicates the first reflected light RY1 reflected by a first retina RE1 corresponding to the first eye EY1. A dashed line in FIG. 2 indicates the second reflected light RY2 reflected by a second retina RE2 corresponding to the second eye EY2. Note that only light rays (principal rays) passing through centers of pupils and marginal rays are illustrated, and illustration of other light rays is omitted.

An intermediate image IF is an image of retinas formed by the first eye EY1 and the second eye EY2 of the subject. At this time, the first retina RE1 and the second retina RE2 are conjugate with the light receiving surface of the imaging device 103. The first reflected light RY1 is condensed by a first crystalline lens PP1 corresponding to the first eye EY1 to form the intermediate image IF, and passes through a first pupil AP1 in a first aperture HO1 of the diaphragm AP to form an image on the light receiving surface of the imaging device 103. Likewise, the second reflected light RY2 is condensed by a second crystalline lens PP2 corresponding to the second eye EY2 to form the intermediate image IF, and passes through a second pupil AP2 in a second aperture HO2 of the diaphragm AP to form an image on the light receiving surface of the imaging device 103.

In the present embodiment, a light flux of the first reflected light RY1 and a light flux of the second reflected light RY2 do not overlap each other when passing through the pupils, and the first pupil AP1 and the second pupil AP2 are present in regions different from each other. The first crystalline lens PP1 (or pupil of first eye EY1) and the second crystalline lens PP2 (or pupil of second eye EY2) are respectively conjugate with the first pupil AP1 and the second pupil AP2. The light flux of the first reflected light RY1 and the light flux of the second reflected light RY2 may partially overlap each other, and the region of the first pupil AP1 and the region of the second pupil AP2 may partially overlap each other. At this time, the diaphragm AP may include one aperture. Further, the optical system 102 can simultaneously guide the first reflected light RY1 and the second reflected light RY2 to the corresponding photoelectric conversion units. In other words, the examination apparatus OS1 according to the present embodiment can simultaneously acquire information on both eyes of the subject.

Figure 3:
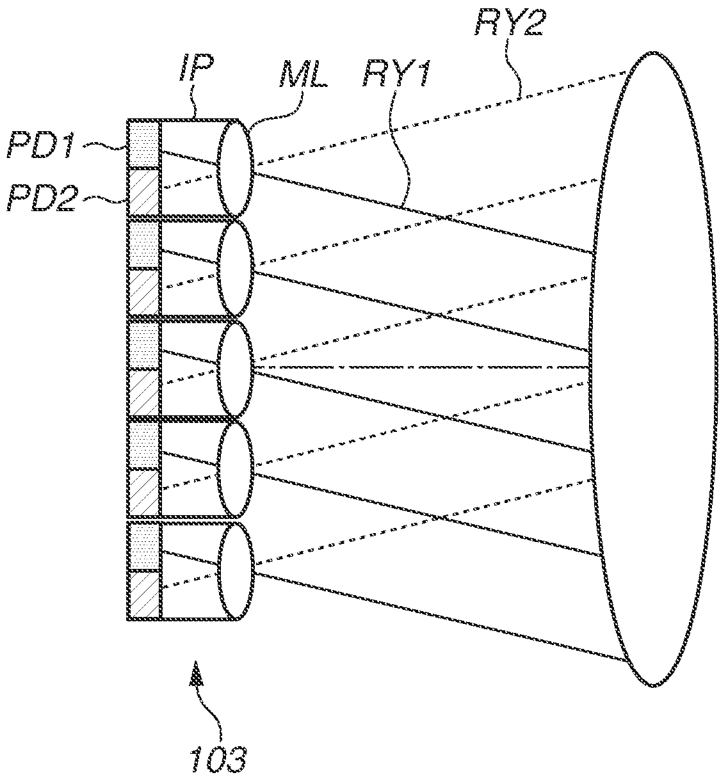
FIG. 3 is a diagram illustrating an imaging device according to the first embodiment.

FIG. 3 illustrates a part of the optical system 102 and the imaging device 103 according to the first embodiment. Out of the first reflected light RY1 and the second reflected light RY2, only light rays passing through centers of the first photoelectric conversion units PD1 and the second photoelectric conversion units PD2 are illustrated, and illustration of other light rays is omitted.

In FIG. 3, the imaging device 103 includes the plurality of pixels IP, and each of the pixels IP includes the microlens ML, the first photoelectric conversion unit PD1, and the second photoelectric conversion unit PD2.

The optical system 102 condenses the first reflected light RY1 and the second reflected light RY2 to the same (common) microlens ML. At this time, the first reflected light RY1 and the second reflected light RY2 enter the microlens ML at incident angles different from each other because the first reflected light RY1 and the second reflected light RY2 pass through the pupils different from each other. More specifically, relative to a normal (alternate long and short dash line) of the imaging surface of the imaging device 103, one of the first reflected light RY1 and the second reflected light RY2 enters the microlens ML from above, and the other reflected light enters the microlens ML from below.

A cross-section including an optical axis of the microlens ML may be regarded as the normal. In other words, in the present embodiment, signs of the incident angles of the first reflected light RY1 and the second reflected light RY2 to the microlens are different from each other.

The microlens ML condenses (causes incidence of) the first reflected light RY1 from the first pupil AP1 to the first photoelectric conversion unit PD1. Likewise, the microlens ML condenses (causes incidence of) the second reflected light RY2 from the second pupil AP2 to the second photoelectric conversion unit PD2. In other words, the optical system 102 causes the first reflected light RY1 and the second reflected light RY2 to form images at the same conjugate position (microlens ML) for the first retina RE1 and the second retina RE2. Further, the microlens ML can guide the first reflected light RY1 to the first photoelectric conversion unit PD1, and guide the second reflected light RY2 to the second photoelectric conversion unit PD2.

The optical system 102 according to the present embodiment condenses the first reflected light RY1 and the second reflected light RY2 having passed through the different pupils to one imaging device 103. Such a configuration makes it possible to guide the first reflected light RY1 and the second reflected light RY2 to the imaging device 103 by one imaging lens. This makes it possible to simplify the optical system.

In a case where an axis passing through a center of a lens configuring the optical system 102 is an optical axis, the examination apparatus OS1 can be installed such that the optical axis and a line segment connecting centers of the first eye EY1 and the second eye EY2 are positioned on the same plane. This makes it possible to enhance accuracy in measurement of the fixation state. At this time, the video image display device preferably presents a relative position of the examination apparatus OS1 and the subject to the user based on image information. In the examination, a line segment connecting the centers of the first and second eyes (or pupils or crystalline lenses), a line segment connecting centers of the first and second pupils, and a line segment connecting centers of the first and second photoelectric conversion units of one pixel are preferably positioned on the same plane.

The optical axis of the microlens ML positioned on a peripheral portion of the imaging device 103 may be made eccentric from a middle position between the first photoelectric conversion unit PD1 and the second photoelectric conversion unit PD2. The optical axis of the microlens ML may be made eccentric to a center side in parallel, from the middle position between the first photoelectric conversion unit PD1 and the second photoelectric conversion unit PD2. An eccentric amount may be varied depending on a region of the imaging device 103.

A light ray that enters a center of the microlens ML of an optional pixel IP and is guided between the first photoelectric conversion unit PD1 and the second photoelectric conversion unit PD2 of the optional pixel IP is regarded as a reference light ray of the optional pixel IP. The reference light ray may be different depending on a position of the pixel IP in the imaging device 103. At this time, an incident angle of the reference light ray entering the microlens ML of the pixel IP positioned on the peripheral portion of the imaging device 103 is preferably greater (more inclined) than an incident angle of the reference light ray entering the microlens ML of the pixel IP positioned at the center of the imaging device 103. The reference light ray entering the microlens ML positioned at the center of the imaging device 103 is parallel to the normal of the imaging surface of the imaging device 103.

Figure 4:
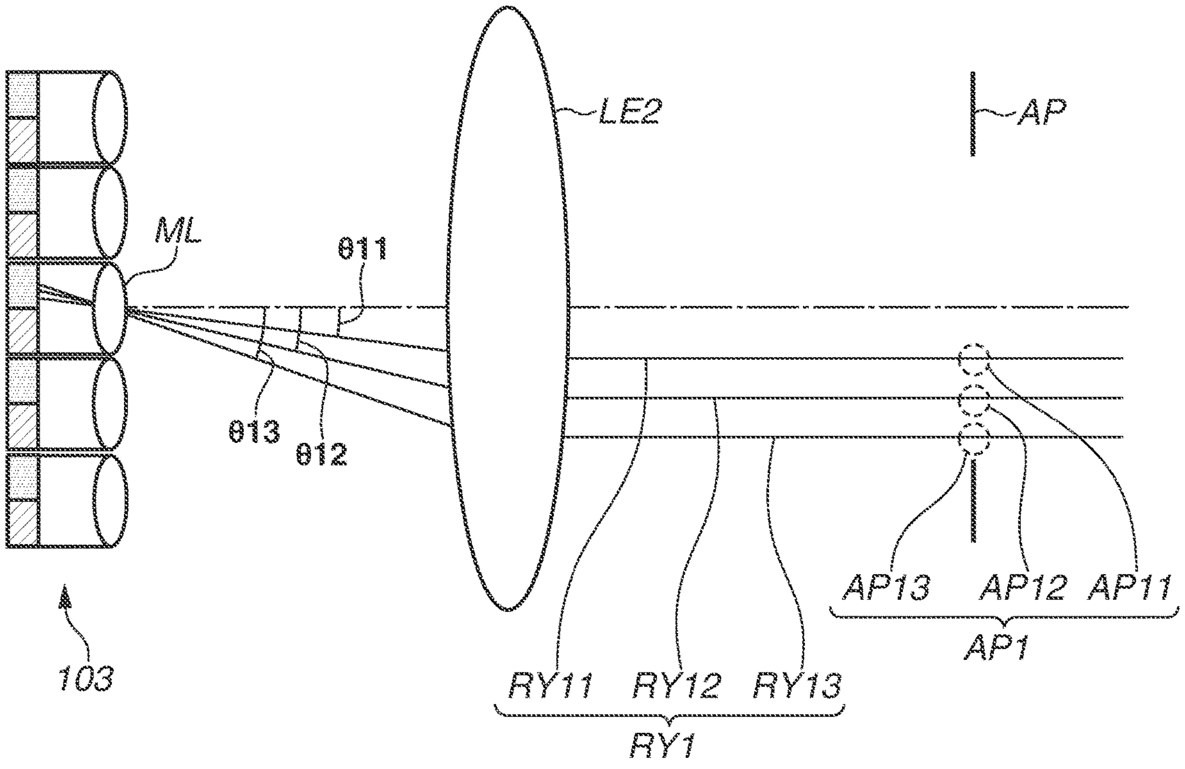
FIG. 4 is a diagram illustrating relationship between positions of pupils and incident angles of reflected light to the imaging device.

FIG. 4 is a diagram illustrating relationship between positions of the pupils of the optical system 102 and incident angles of the reflected light to the imaging device 103. In FIG. 4, out of the first reflected light RY1, light rays passing through the pupil AP1 and the microlens ML positioned on the optical axis of the optical system 102 are illustrated, and illustration of other light rays is omitted.

In FIG. 4, the pupil AP1 is positioned on the diaphragm AP (diaphragm surface) disposed perpendicularly to the normal (optical axis) of the microlens ML positioned on the optical axis. A pupil AP11, a pupil AP12, and a pupil AP13 are different in distance from the optical axis, and distances of the respective pupils are denoted by LAP11, LAP12, and LAP13. Light rays of the first reflected light RY1 passing through the pupil AP11, the pupil AP12, and the pupil AP13 are denoted by RY11, RY12, and RY13.

The light rays RY11, RY12, and RY13 are condensed to the microlens ML through the optical device LE2. Incident angles of the light rays RY11, RY12, and RY13 to the microlens ML are denoted by θ11, θ12, and θ13.

In FIG. 4, distances from an intersection of the normal of the microlens ML (or reference light ray) and the diaphragm AP to the respective pupils become larger in order of AP11, AP12, and AP13. The incident angles of the light rays to the microlens ML becomes larger in order of θ11, θ12, and θ13. In other words, the light ray passing through the pupil larger in distance from the normal of the imaging surface has a larger absolute value of the incident angle to the microlens ML.

Figure 5:
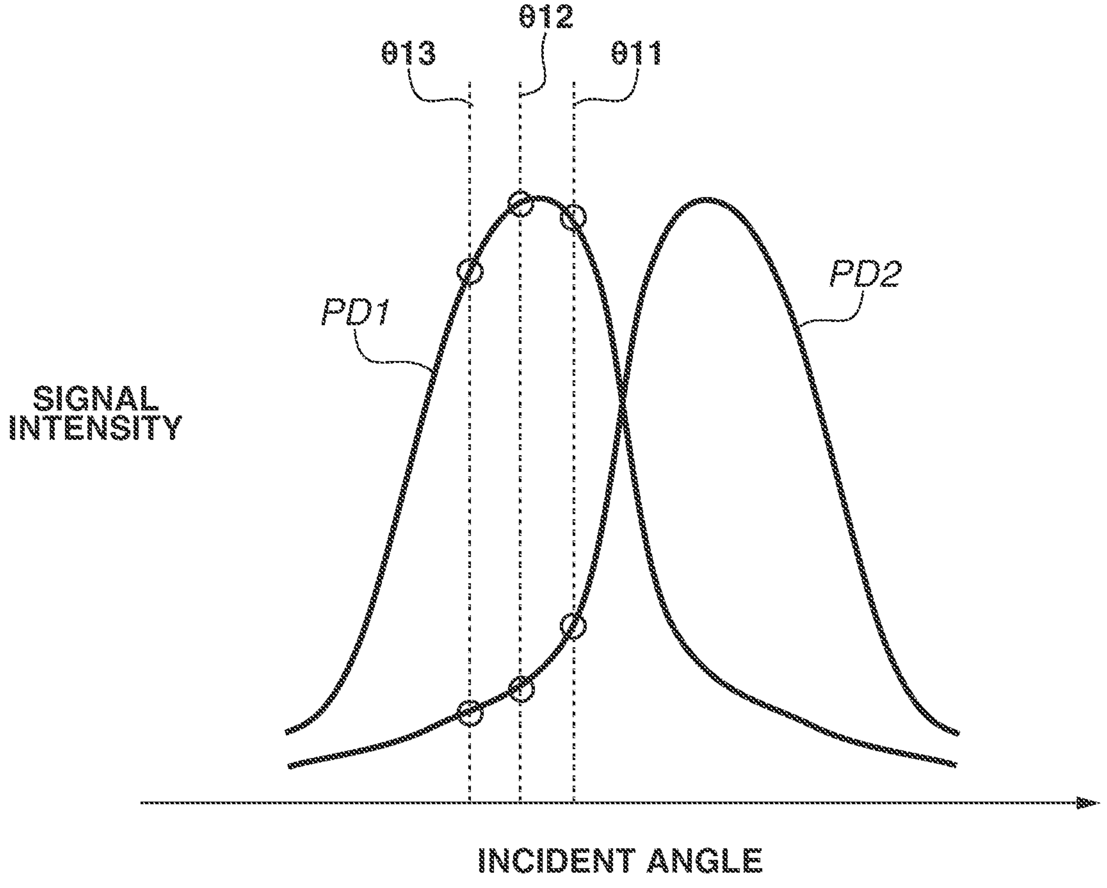
FIG. 5 is a diagram illustrating relationship between signal intensity and an incident angle of a light ray to the imaging device, of each of photoelectric conversion units.

Characteristics of the imaging device 103 according to the present embodiment will now be described. FIG. 5 is a diagram illustrating distribution of signal intensity (signal intensity distribution) to the incident angle of the light ray to the imaging device 103, obtained by each of the photoelectric conversion units. A vertical axis in FIG. 5 indicates the signal intensity corresponding to light receiving sensitivity of the first photoelectric conversion unit PD1 or the second photoelectric conversion unit PD2. A horizontal axis in FIG. 5 indicates the incident angles of the first reflected light RY1 and the second reflected light RY2 to the microlens ML. An incident angle side on which the signal intensity becomes the maximum in the signal intensity distribution of the first photoelectric conversion unit PD1 is represented as negative, and an incident angle side on which the signal intensity becomes the maximum in the signal intensity distribution of the second photoelectric conversion unit PD2 is represented as positive. A value of the horizontal axis is standardized based on an intersection of the signal intensity distribution of the first photoelectric conversion unit PD1 and the signal intensity distribution of the second photoelectric conversion unit PD2. FIG. 5 illustrates the signal intensities at the incident angles θ11, θ12, and θ13. The standardization may be performed while an incident angle of the reference light ray to an optional pixel is used as a reference, and an intersection of the signal intensity distribution of the first photoelectric conversion unit PD1 and the signal intensity distribution of the second photoelectric conversion unit PD2 is associated with the incident angle. As an example, in the present embodiment, the incident angle at which the signal intensity of the first photoelectric conversion unit PD1 becomes the maximum is set to θ12.

In the present embodiment, the signs of the incident angles of the first reflected light RY1 and the second reflected light RY2 to the microlens ML are different from each other. However, in FIG. 5, the first photoelectric conversion unit PD1 photoelectrically converting the first reflected light RY1 performs photoelectric conversion irrespective of the sign of the incident angle. This is influence of crosstalk generated between the photoelectric conversion units disposed adjacent to each other. In the second photoelectric conversion unit PD2, crosstalk is also generated in a manner similar to the first photoelectric conversion unit PD1. A crosstalk amount generated in each of the first photoelectric conversion unit PD1 and the second photoelectric conversion unit PD2 is varied depending on the incident angle to the imaging device 103 (or microlens ML). Therefore, the examination apparatus OS1 according to the present embodiment can correct influence of the crosstalk based on the incident angle to the microlens ML. The crosstalk amount may be represented by a ratio of the signal intensity of the first photoelectric conversion unit PD1 and the signal intensity of the second photoelectric conversion unit PD2.

The crosstalk in the present embodiment includes at least one of optical crosstalk generated by stray light caused by reflection and scattering in the microlens, a wiring layer, and the like, and electric crosstalk generated by movement of charges to adjacent another photoelectric conversion unit.

The signal intensities of the first photoelectric conversion unit PD1 and the second photoelectric conversion unit PD2 are respectively denoted by PD1S and PD2S, and the crosstalk amounts generated in the first photoelectric conversion unit PD1 and the second photoelectric conversion unit PD2 are respectively denoted by CT1 and CT2. In addition, when corrected signal intensities (correction signal intensities) corresponding to the first photoelectric conversion unit PD1 and the second photoelectric conversion unit PD2 are respectively denoted by PD1S' and PD2S', relationship can be represented by expressions (2a) and (2b):

$$PD1S' = PD1S - PD2S \times CT1, \tag{2a}$$

$$PD2S' = PD2S - PD1S \times CT2. \tag{2b}$$

As described above, in the present embodiment, by using the above-described expressions (2a) and (2b), correction signals under less influence of the crosstalk generated between the photoelectric conversion units is suppressed can be acquired based on the signal intensities of the first photoelectric conversion unit PD1 and the second photoelectric conversion unit PD2, and the crosstalk amounts.

In the relationship of the signal intensity to the incident angle to the imaging device 103 as illustrated in FIG. 5, the signal intensity obtained by each of the photoelectric conversion units is increased as the incident angle is increased up to a certain angle (θ12 in FIG. 5). In contrast, in a case where the incident angle is further increased beyond the certain angle (θ12 in FIG. 5), the signal intensity obtained by each of the photoelectric conversion units is reduced.

Therefore, when the light ray angle (incident angle) of the first reflected light RY1 and the second reflected light RY2 condensed to the imaging device 103 via the optical system 102 to the optical axis is denoted by θ[°], the incident angle of the light ray entering the imaging device 103 according to the present embodiment preferably satisfies the following conditional inequality (3):

$$0 \leq |\theta| \leq 35. \tag{3}$$

In a case where the angle θ becomes greater than an upper limit of the conditional inequality (3), the signal intensity obtained by each of the photoelectric conversion units is reduced. Therefore, a signal-to-noise ratio (SN ratio) of the signal acquired by each of the photoelectric conversion units is reduced, which may deteriorate examination accuracy.

Further, the incident angle of the light ray entering the imaging device 103 preferably satisfies the following conditional inequality (3a), and more preferably satisfies the conditional inequality (3b):

$$0 \leq |\theta| \leq 30, \tag{3a}$$

$$0 \leq |\theta| \leq 25. \tag{3b}$$

Note that a relative inclination to the reference light ray varied for each of the microlens ML of the imaging device 103 may be regarded as the incident angle.

The incident angle varies based on an image-side F-number of the optical system. The image-side F-number can be adjusted by the diaphragm AP of the optical system 102 and by arranging a diaphragm (first diaphragm) for shielding a most off-axis light flux (light flux reaching most off-axis image height) separately from the diaphragm AP. It is sufficient for the first diaphragm to limit an off-axis light flux (to shield part of off-axis light flux).

Figures 6A, 6B, 6C:
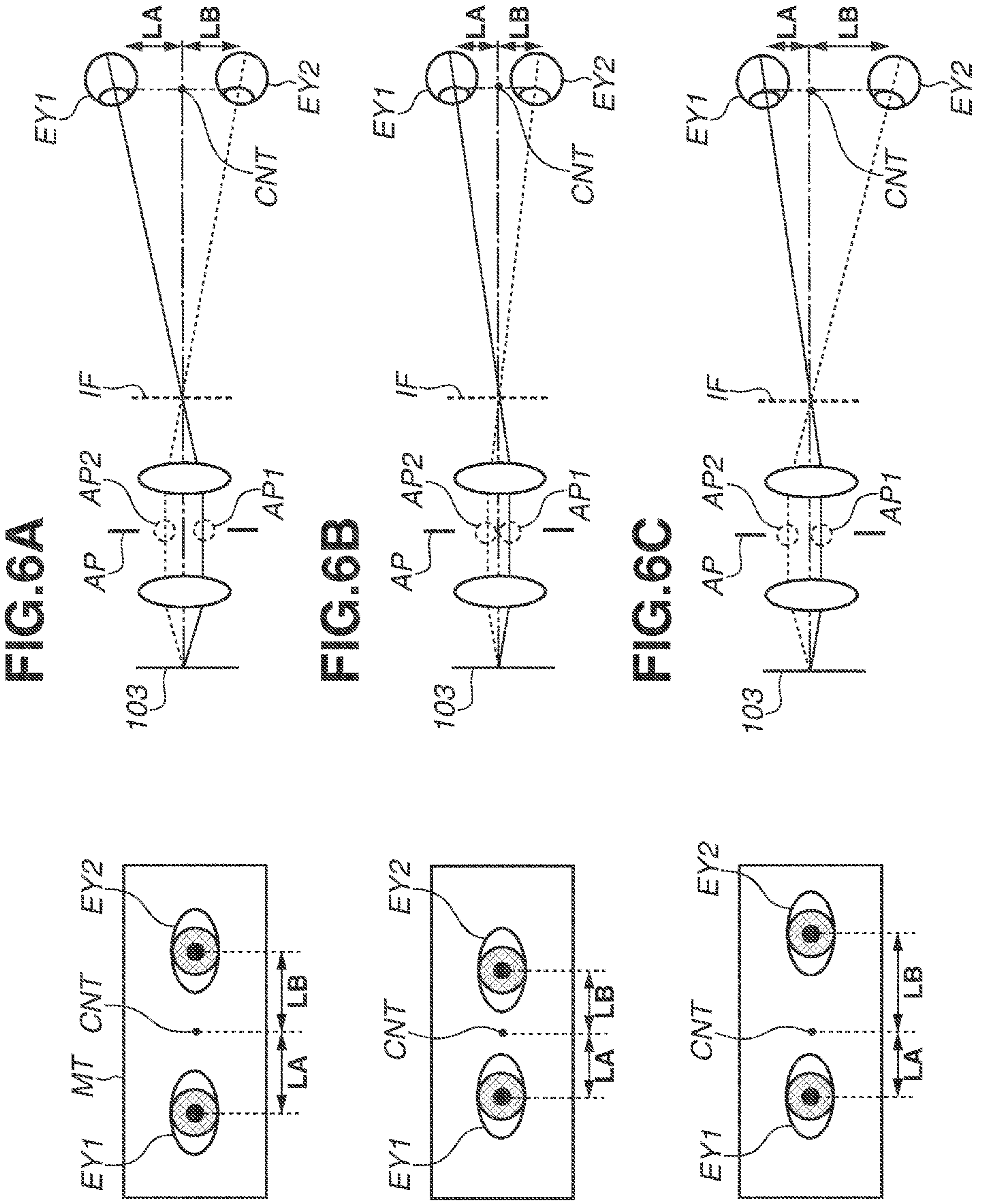
FIGS. 6A, 6B, and 6C are diagrams illustrating estimation of positions of the pupils.

A method of estimating the positions of the pupils will be described with reference to FIGS. 6A to 6C. FIGS. 6A to 6C each illustrate relationship between the examination apparatus OS1 according to the first embodiment and the subject, and an example of the video image information MT displayed on the video image display device in the relationship. The video image information MT according to the present embodiment is generated based on the image information.

A middle point CNT in FIGS. 6A to 6C is an intersection of the normal (alternate long and short dash line) of the imaging surface of the imaging device and a line segment (alternate long and two short dashes line) connecting the first eye EY1 and the second eye EY2. An intersection of the line segment connecting the first eye EY1 and the second eye EY2 and the reference light ray guided to the imaging device 103 may be regarded as the point CNT. At this time, the line segment connecting the first eye EY1 and the second eye EY2 is parallel to an arrangement direction of the first photoelectric conversion unit PD1 and the second photoelectric conversion unit PD2 included in each pixel IP. Further, a distance (first distance) from the middle point CNT to the first eye EY1 is denoted by LA, and a distance (second distance) from the middle point CNT to the second eye EY2 is denoted by LB. In the present embodiment, the first distance LA and the second distance LB are the distances from the middle point CNT to the first and second eyes, but may be information at least about distances to the first and second eyes. For example, the first distance LA and the second distance LB each may be a distance from the middle point CNT to a center or an end of the corresponding eye. Further, the first distance LA and the second distance LB each may be a distance from the middle point CNT to a center of the corresponding pupil or crystalline lens. Further, information obtained by four arithmetic operations based on the distances from the middle point CNT to the first and second eyes may be used.

As illustrated in FIGS. 6A to 6C, the positions of the pupils of the optical system 102 through which the reflected light from the corresponding eyes passes are farther away from the optical axis as the first distance LA and the second distance LB are increased.

In FIG. 6A, the pupils of the first eye EY1 and the second eye EY2 are respectively conjugate with the first pupil AP1 and the second pupil AP2 on the diaphragm AP of the optical system 102. Therefore, the positions of the first pupil AP1 and the second pupil AP2 are estimated based on the distances from the middle point CNT to the first and second eyes (first distance LA ad second distance LB).

As illustrated in FIG. 4, the incident angle to the imaging device 103 is associated with the positions of the first pupil AP1 and the second pupil AP2. Therefore, the incident angle to the imaging device 103 is estimated based on the positions of the first pupil AP1 and the second pupil AP2. Alternatively, the incident angle to the imaging device 103 may be estimated based on the distances from the middle point CNT to the first and second eyes (first distance LA and second distance LB).

Further, as illustrated in FIG. 5, the crosstalk amounts are associated with the incident angle to the imaging device 103. Therefore, the crosstalk amounts can be acquired based on the incident angle to the imaging device 103. The incident angle to the imaging device 103 is acquired based on the distances from the middle point CNT to the first and second eyes. Therefore, the processing unit 105 (third acquisition unit) can acquire the crosstalk amounts based on the information about the positions of the first and second eyes.

In FIG. 6B, the first distance LA and the second distance LB are shorter than those in FIG. 6A. In FIG. 6C, the first distance LA and the second distance LB are not equal to each other. Even in a case of FIG. 6B and FIG. 6C, the positions of the first pupil AP1 and the second pupil AP2 of the optical system 102, and the incident angle to the imaging device 103 can be estimated based on the first distance LA and the second distance LB.

Table 1 illustrates an example of a conversion table for converting the information about the positions of the first and second eyes to the crosstalk amounts according to the present embodiment. Table 1 is an example of a conversion table for deriving the crosstalk amounts from the distances from the middle point CNT to the eyes according to the present embodiment.

Table 1 illustrates relationship of the position of the corresponding pupil, the incident angle to the imaging device, and the crosstalk amount relative to the distance from the middle point CNT to one eye. The number of divisions of the conversion table is not limited to the number in Table 1. For example, the values, and the intervals and the number of divisions of the distances from the middle point CNT to the first and second eyes may be changed based on the characteristics of the optical system 102, the characteristics of the imaging device 103, and the like. As necessary, the conversion table may be changed based on the wavelength of the light emitted from the illumination unit 101, the incident angle to the pixel positioned on the peripheral portion of the imaging device 103, the crosstalk amount between adjacent pixels, and characteristics of the first photoelectric conversion unit PD1 and the second photoelectric conversion unit PD2.

The crosstalk amounts may be acquired solely from the distances from the middle point CNT to the first and second eyes without determining the distances from the optical axis to the pupils and the incident angle. At this time, the conversion table determined based on the characteristics of the optical system 102, the characteristics of the imaging device 103, and the like can be used. Such a configuration makes it possible to reduce a processing amount of the calculation by the processing unit 105.

The examination apparatus OS1 according to the present embodiment may include a storage unit storing the conversion table.

TABLE 1

| Distance from Middle Point CNT to Eye | Distance from Optical Axis to Pupil | Incident Angle [°] | Crosstalk Amount [%] |
|---|---|---|---|
| L1 | LAP1 | θ1 | 30 |
| L2 | LAP2 | θ2 | 25 |
| L3 | LAP3 | θ3 | 20 |
| L4 | LAP4 | θ4 | 15 |
| L5 | LAP5 | θ5 | 10 |

Figure 7:
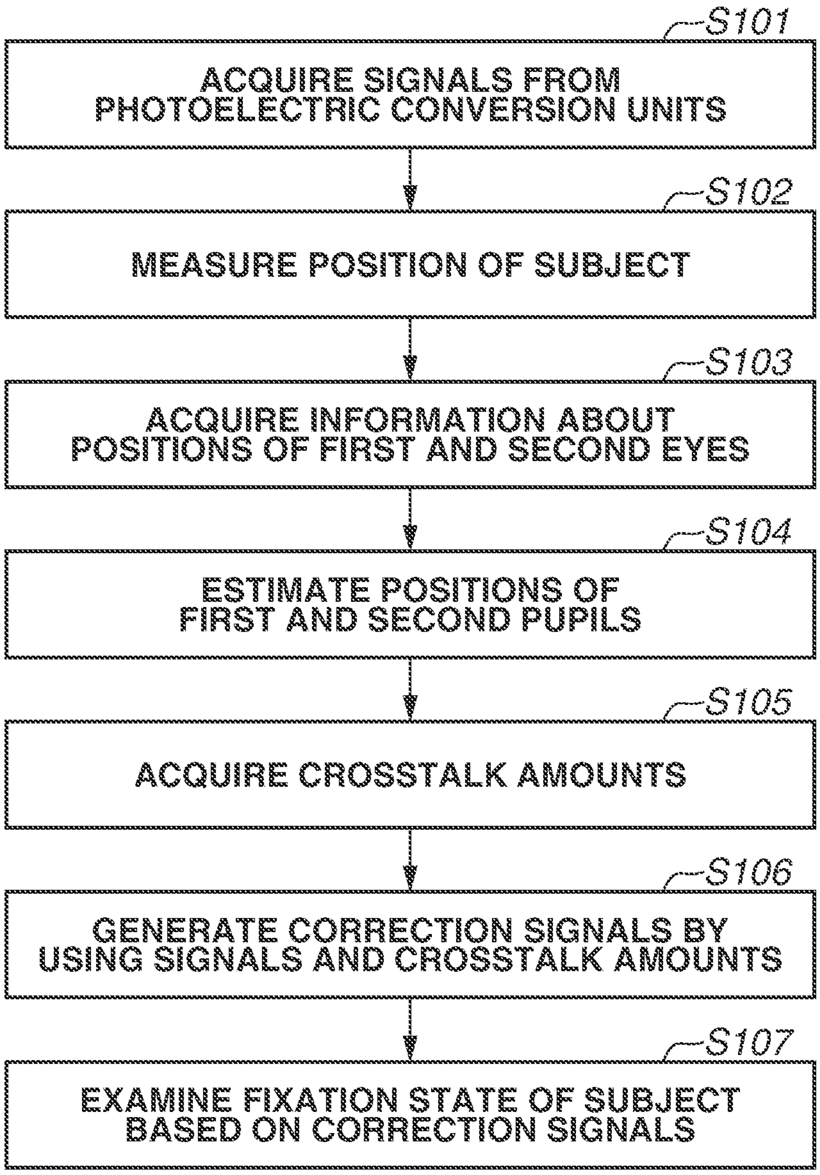
FIG. 7 is a flowchart illustrating one mode of processing by the examination apparatus.

FIG. 7 is a flowchart illustrating one mode of the processing according to the present embodiment. In step S101, the first acquisition unit 105*a* acquires the signals (intensities) from the first photoelectric conversion units PD1 and the second photoelectric conversion units PD2. The signals at this time include errors of the crosstalk of the first photoelectric conversion units PD1 and the second photoelectric conversion units PD2. The acquired signals are information based on the reflected light from the right and left eyes. The first acquisition unit 105*a* can separate the signals corresponding to the first reflected light RY1 and the second reflected light RY2 into information corresponding to the right eye and the left eye. In other words, the first acquisition unit 105*a* can acquire a first signal based on the first reflected light entering the first photoelectric conversion units, and a second signal based on the second reflected light entering the second photoelectric conversion units. In a case where the optical system 102 includes the optical device relating to polarization, the first acquisition unit 105*a* can separate and acquire signals corresponding to reflected light different in polarization state.

In step S102, the measurement unit 104 measures the position of the subject. The measurement of the position of the subject by the measurement unit 104 can be performed using a known image processing method or ranging method. At this time, the signals acquired by the first photoelectric conversion units PD1 and the second photoelectric conversion units PD2 may be used.

In step S103, the second acquisition unit 105*b* acquires the information about the positions of the first and second eyes. In the present embodiment, as the information about the positions of the first and second eyes, the distances from the middle point CNT to the center of the pupil of the first eye EY1 and to the center of the pupil of the second eye EY2 are acquired.

The information about the positions of the first and second eyes is not limited thereto. For example, the distances from the imaging device 103 to the first and second eyes may be used as the information about the positions of the first and second eyes.

The information about the positions of the first and second eyes may be acquired using the above-described information about the distance to the subject. When the information about the positions of the first and second eyes is acquired using the information about the distance to the subject, it is possible to enhance accuracy of the information about the positions of the first and second eyes. The information about the positions of the first and second eyes is acquired by, for example, image processing based on the image information included in the signals converted by the photoelectric conversion units. Note that the acquisition method is not limited thereto.

The first photoelectric conversion units PD1 and the second photoelectric conversion units PD2 of the pixels IP are preferably disposed in parallel to the line segment connecting the first eye EY1 and the second eye EY2. Such a configuration makes it possible to enhance detection accuracy of the information about the positions of the first and second eyes by the second acquisition unit 105*b*.

In a case where the information about the distance to the subject is not used, the processing in step S102 may not be performed. The processing in step S102 and step S103 may be processed as one step.

In step S104, the estimation unit 105*e* estimates the positions of the pupils on the diaphragm AP of the optical system 102 or the incident angles of the first reflected light RY1 and the second reflected light RY2 to the imaging device 103 based on the information about the positions of the first and second eyes as necessary. The estimation unit 105*e* may estimate both of the positions of the pupils on the diaphragm AP of the optical system 102 and the incident angles of the first reflected light RY1 and the second reflected light RY2 to the imaging device 103.

In step S105, the third acquisition unit 105*c* acquires the crosstalk amounts generated in the first photoelectric conversion units PD1 and the second photoelectric conversion units PD2 based on the information about the positions of the first and second eyes. In the present embodiment, the crosstalk amounts are acquired using the above-described conversion table. Note that the acquisition method is not limited thereto. The crosstalk amounts may be acquired using, for example, a function. Such a configuration makes it possible to determine the crosstalk amounts as continuous values without increasing a capacity of the conversion table stored in the storage unit. Therefore, it is possible to enhance accuracy of the calculation for determining the crosstalk amounts.

In step S106, the processing unit 105*d* acquires the correction signals based on the signals acquired by the first acquisition unit 105*a* and the crosstalk amounts acquired by the third acquisition unit 105*c*. At this time, the correction signals can be calculated using the above-described expressions (2a) and (2b). Such a configuration makes it possible to acquire signals (correction signals) that are reduced in influence of the crosstalk from the signals obtained by the photoelectric conversion. The processing unit 105 (or processing unit 105*d*) acquires at least one of the image information, the luminance information, and the information on the polarization states based on the correction signals. The correction signals reduced in influence of the crosstalk are acquired from the signals corresponding to the reflected light from the first eye EY1 and the second eye EY2, it is possible to enhance examination accuracy of the fixation state of the subject.

In step S107, the processing unit 105 performs processing for examining (acquiring) the fixation state of the subject based on the correction signals. The examination of the fixation state based on the information acquired using the optical system and the imaging device can be performed by using, for example, a method discussed in Japanese Unexamined Patent Application Publication (Translation of PCT Application) No. 2018-509203.

The processing in the flowchart according to the present embodiment is not limited thereto, and for example, the calculation for the eyes EY1 and EY2 may be sequentially performed in an optional order.

Figure 8:
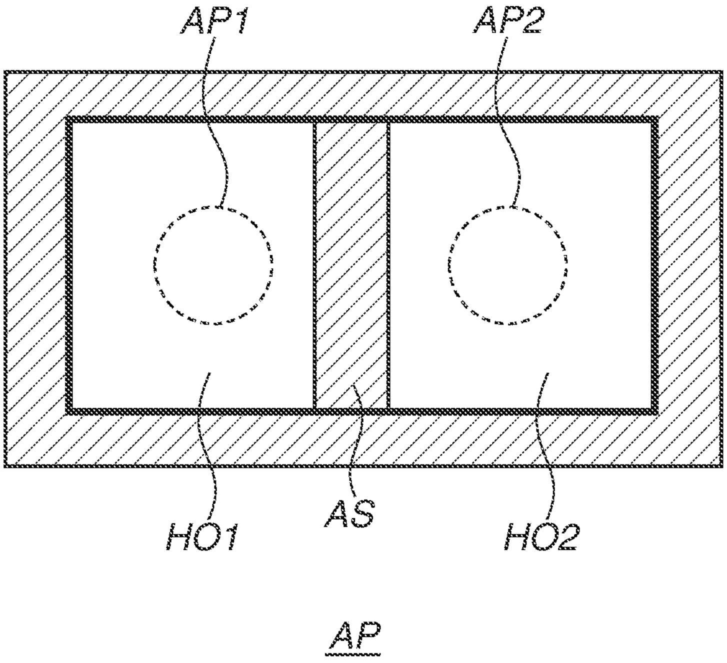
FIG. 8 is a diagram illustrating a diaphragm as viewed from an object side of an optical system.

FIG. 8 is a diagram illustrating the diaphragm AP as viewed from the object side of the optical system 102. The diaphragm AP is a light shielding member including apertures. In the present embodiment, the diaphragm AP includes the aperture HO1 and the aperture HO2. A boundary between the aperture HO1 and the aperture HO2 of the diaphragm AP is defined by a center light shielding portion AS as a light shielding member. The center light shielding portion AS shields unnecessary light (ghost light) at the boundary between the aperture HO1 and the aperture HO2. The first reflected light RY1 passes through the first pupil AP1 in the first aperture HO1, and the second reflected light RY2 passes through the second pupil AP2 in the second aperture HO2. Such a configuration makes it possible to reduce unnecessary light (ghost light) reflected inside the examination apparatus OS1. In FIG. 8, the first aperture HO1 and the second aperture HO2 of the diaphragm AP each have a rectangular shape; however, the shape of each of the apertures is not limited thereto, and may be an elliptical shape or the like.

In place of the diaphragm AP, an optical device having an effect similar to the effect of the diaphragm AP may be disposed. More specifically, a light shielding film may be provided on an optical plane of the optical device to form the first aperture HO1 and the second aperture HO2. The light shielding member is used at the boundary between the first aperture HO1 and the second aperture HO2, which makes it possible to effectively suppress unnecessary light.

Figure 9:
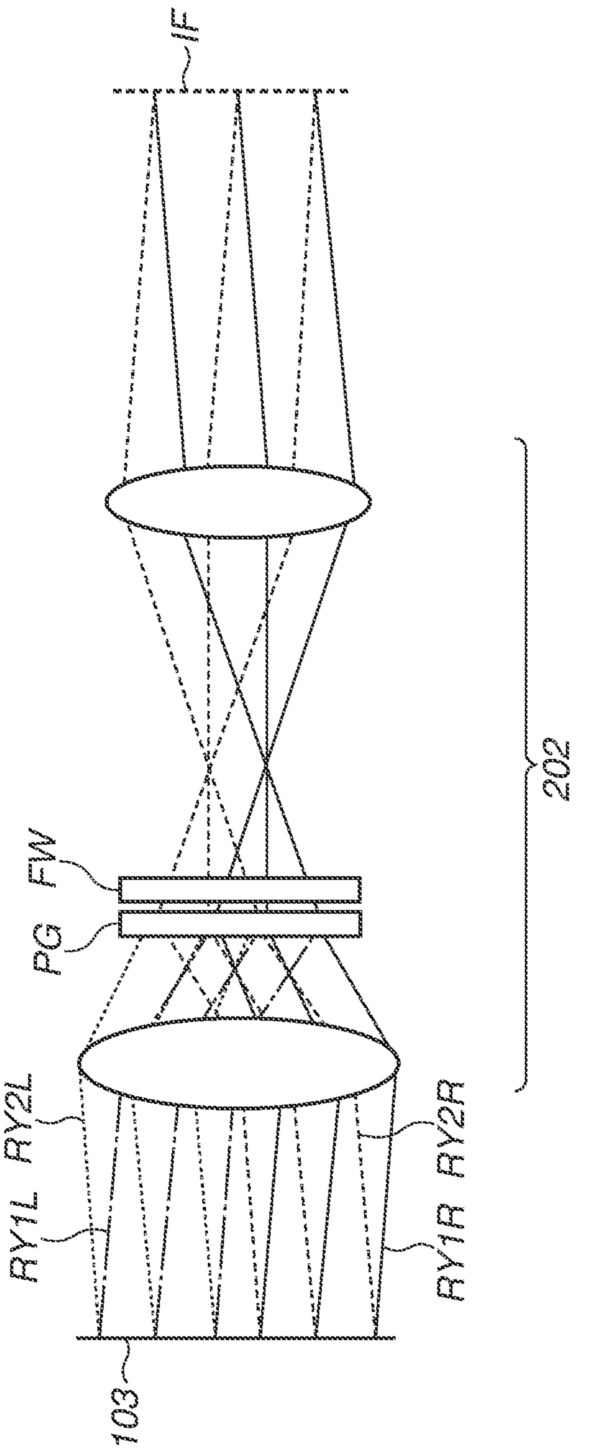
FIG. 9 is a schematic view illustrating main portions of an examination apparatus according to a second embodiment.

FIG. 9 is a schematic view illustrating main portions of an examination apparatus OS2 according to a second embodiment. The examination apparatus OS2 according to the present embodiment is different from the examination apparatus OS1 according to the first embodiment in that a polarization element changing polarization states of the first reflected light RY1 and the second reflected light RY2 is disposed in an optical system 202.

Further, the examination apparatus OS2 according to the present embodiment includes a second light source. The second light source is a light source (fixation lamp) emitting light that direct visual lines of the subject to the examination apparatus OS2. As the second light source, a display member such as a liquid crystal display and an organic EL display, and one or a plurality of point light sources such as laser diodes may be disposed. A wavelength of the light emitted from the second light source is preferably within a visible range visually recognizable by the subject during the examination. Such a configuration makes it possible to cause the subject to pay attention to (turn eyes on) the examination apparatus OS2, and to perform examination more rapidly.

The optical system 202 may include a beam splitter as necessary. The beam splitter according to the present embodiment reflects the light emitted from the second light source to the object side. On the other hand, the beam splitter allows the reflected light reflected by the retinas to pass therethrough. When the beam splitter is used, the optical system guiding the light emitted from the second light source and the optical system (imaging optical system) guiding the first reflected light RY1 and the second reflected light RY2 to the imaging device 103 can be partially made common. This makes it possible to downsize the optical system 202 and the examination apparatus OS2.

In the present embodiment, as the polarization element changing the polarization states, a ¼ wavelength plate FW and a polarization diffraction element PG are used. The ¼ wavelength plate FW separates the first reflected light RY1 into a light flux RY1R in a first phase state and a light flux RY1L in a second phase state. Likewise, the ¼ wavelength plate FW separates the second reflected light RY2 into a light flux RY2R in the first phase state and a light flux RY2L in the second phase state.

The processing unit 105 according to the present embodiment can measure birefringent properties of the retinas from change of the polarization states of the illumination light to the retinas and the reflected light from the retinas, and can separate the acquired signals into information on a plurality of polarization states for each of the right and left eyes.

In the present embodiment, the light flux in the first phase state and the light flux in the second phase state are light fluxes having a phase difference of 90 degrees from each other. The polarization element is not limited thereto, and a ⅛ wavelength plate or a ½ wavelength plate may be used. The light entering the polarization diffraction element PG is diffracted by the polarization diffraction element PG depending on the polarization state of the light. The reflected light from the retinas is detected using the polarization element, which makes it possible to measure the birefringent properties at the reflected positions.

In the present embodiment, the first reflected light RY1 and the second reflected light RY2 having passed through the different pupils can be condensed to one imaging device 103, and the first reflected light RY1 and the second reflected light RY2 can be photoelectrically converted by the imaging device 103 alone, as in the first embodiment. Therefore, the optical system can be simplified. Further, since the polarization element is disposed in the optical system 202, it is possible to change the specific polarization states of the first reflected light RY1 and the second reflected light RY2. Accordingly, the birefringent properties of the retinas can be measured, and the fixation state of the eyes can be examined with higher accuracy.

In FIG. 9, the optical system 202 separates the first reflected light RY1 and the second reflected light RY2 such that the positions (microlens ML) where the light flux RY1R and the light flux RY2R form images and the positions (microlens ML) where the light flux RY1L and the light flux RY2L form images do not overlap with each other; however, the positions may partially overlap with each other. In other words, the light fluxes in the different phase states separated from the same reflected light may be condensed to the same position (microlens ML) at the same incident angle. At this time, the light fluxes RY1R, RY1L, RY2R, and RY2L guided to the same photoelectric conversion units by the microlens ML can be converted into signals in a time division manner (by using time sharing). Alternatively, signals may be separated from the two overlapped light fluxes by image processing and the like. The processing is performed by the processing unit 105.

Although the preferred embodiments of the present disclosure are described above, the present disclosure is not limited to these embodiments, and may be variously modified and changed within the scope of the gist.

OTHER EMBODIMENTS

Embodiment(s) of the present disclosure can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present disclosure has been described with reference to embodiments, it is to be understood that the disclosure is not limited to the disclosed embodiments. The scope of the following claims is to be accorded the broadest interpretation so as to encompass all such modifications and equivalent structures and functions.

This application claims the benefit of priority from Japanese Patent Application No. 2023-036747, filed Mar. 9, 2023, which is hereby incorporated by reference herein in its entirety.

What is claimed is:

1. An examination apparatus detecting first reflected light from a first eye of a subject and second reflected light from a second eye of the subject, the examination apparatus comprising:

an imaging device; and a processing unit, wherein the imaging device includes pixels each including a first photoelectric conversion unit and a second photoelectric conversion unit, and wherein the processing unit includes:

one or more memories storing instructions; and at least one processor configured to execute the instructions to cause the processing unit to:

acquire a first signal based on the first reflected light entering the first photoelectric conversion units and a second signal based on the second reflected light entering the second photoelectric conversion units, acquire crosstalk amounts of the first and second signals based on information about positions of the first and second eyes, and generate correction signals based on the first and second signals and amounts of the crosstalk.

2. The examination apparatus according to claim 1, further comprising an optical system, wherein each of the pixels includes a microlens, wherein the optical system condenses the first reflected light to the microlenses via a first pupil, and condenses the second reflected light to the microlenses via a second pupil, and wherein the microlenses cause the first reflected light to enter the respective first photoelectric conversion units, and cause the second reflected light to enter the respective second photoelectric conversion units.

3. The examination apparatus according to claim 2, wherein the optical system causes the first and second reflected light to enter each of the microlenses from sides different from each other relative to a cross-section including an optical axis of the microlens.

4. The examination apparatus according to claim 1, wherein the information about the positions of the first and second eyes is information about a distance from an intersection of a normal of an imaging surface of the imaging device and a line segment connecting the first eye to the second eye.

5. The examination apparatus according to claim 2, wherein an intermediate image of the first eye is formed between the optical system and the first eye, and an intermediate image of the second eye is formed between the optical system and the second eye.

6. The examination apparatus according to claim 1, wherein the information about the positions of the first and second eyes is acquired based on the first and second signals.

7. The examination apparatus according to claim 1, wherein the information about the positions of the first and second eyes is acquired based on information about a distance to the subject.

8. The examination apparatus according to claim 7, further comprising a measurement unit configured to measure a distance from an imaging surface of the imaging device to the subject.

9. The examination apparatus according to claim 1, wherein the processing unit includes an estimation unit configured to estimate at least one of positions of first and second pupils and incident angles of the first and second reflected light to an imaging surface of the imaging device, based on the information about the positions of the first and second eyes.

10. The examination apparatus according to claim 1, wherein the unit configured to acquire the crosstalk amounts acquires the crosstalk amounts by using a conversion table for converting the information about the positions of the first and second eyes into the crosstalk amounts.

11. The examination apparatus according to claim 1, wherein a following conditional inequality is satisfied, $$0 \leq |\theta| \leq 35,$$

where θ[°] is the incident angle of each of the first and second reflected light to an imaging surface of the imaging device.

12. The examination apparatus according to claim 5, wherein the optical system forms the intermediate image of the first eye and the intermediate image of the second eye on an imaging surface of the imaging device.

13. The examination apparatus according to claim 2, wherein the optical system includes a polarization element configured to change polarization states of the first and second reflected light.

14. The examination apparatus according to claim 2, further comprising:

an illumination unit configured to emit illumination light; and an illumination optical system configured to guide the illumination light to the first and second eyes of the subject.

15. The examination apparatus according to claim 14, wherein a following conditional inequality is satisfied, $$780 \leq \lambda \leq 930,$$

where λ [nm] is a wavelength of the illumination light.

16. The examination apparatus according to claim 14, wherein the optical system and the illumination optical system include a common optical device.

17. The examination apparatus according to claim 1, wherein the processing unit acquires at least one of image information, luminance information, and information on polarization states based on the correction signals.

18. The examination apparatus according to claim 1, wherein the processing unit examines a fixation state of the subject based on the correction signals.

* * * * *